United States Patent [19]
Platt et al.

[11] Patent Number: 5,634,468
[45] Date of Patent: Jun. 3, 1997

[54] SENSOR PATCH AND SYSTEM FOR PHYSIOLOGICAL MONITORING

[75] Inventors: Harry L. Platt, Maroubra; Bruce R. Satchwell, Pennant Hills, both of Australia

[73] Assignee: Micromedical Industries Limited, Labrador, Australia

[21] Appl. No.: 313,054

[22] PCT Filed: Apr. 2, 1993

[86] PCT No.: PCT/AU93/00143

§ 371 Date: Dec. 6, 1994

§ 102(e) Date: Dec. 6, 1994

[87] PCT Pub. No.: WO93/19667

PCT Pub. Date: Oct. 14, 1993

[30] Foreign Application Priority Data

| Apr. 3, 1992 | [AU] | Australia | PL1706 |
| Oct. 20, 1992 | [AU] | Australia | PL5390 |

[51] Int. Cl.⁶ ............ A61B 5/0402; A61B 5/0452
[52] U.S. Cl. .......... 128/696; 128/640; 128/903; 128/736
[58] Field of Search ............ 128/696, 903, 128/640, 633, 736

[56] References Cited

U.S. PATENT DOCUMENTS

| 3,195,534 | 7/1965 | Bethke | 128/206 |
| 3,603,881 | 9/1971 | Thornton | 325/30 |
| 3,902,478 | 9/1975 | Konopasek et al. | 128/2.06 F |
| 3,943,918 | 3/1976 | Lewis | 128/2.1 A |
| 3,960,140 | 6/1976 | Buxton | 128/903 |
| 4,121,573 | 10/1978 | Corvella et al. | 128/2.1 A |
| 4,411,272 | 10/1983 | Phelps, Sr. | 128/711 |
| 4,531,527 | 7/1985 | Reinhold, Jr. et al. | 128/696 |
| 4,709,704 | 12/1987 | Lukaisewicz | 128/644 |
| 4,747,413 | 5/1988 | Bloch | 128/736 |
| 4,791,933 | 12/1988 | Asai | 128/540 |
| 4,865,044 | 9/1989 | Wallace et al. | 128/736 |
| 4,958,645 | 9/1990 | Cadell et al. | 128/696 |
| 5,050,612 | 9/1991 | Matsumura | 128/696 |
| 5,168,874 | 12/1992 | Segalowitz | 128/903 |
| 5,205,297 | 4/1993 | Montecalvo et al. | 128/798 |
| 5,226,431 | 7/1993 | Bible et al. | 128/696 |
| 5,257,631 | 11/1993 | Wilk | 128/696 |
| 5,458,124 | 10/1995 | Stanko et al. | 128/696 |

FOREIGN PATENT DOCUMENTS

| 06230A1 | 2/1992 | European Pat. Off. | 128/696 |
| 293560 | 12/1953 | France . | |
| 2315064 | 3/1973 | Germany . | |
| 2003276 | 3/1979 | United Kingdom . | |
| 2149918 | 6/1985 | United Kingdom | 128/696 |
| 168817 | 6/1986 | United Kingdom | 128/696 |
| 2181554 | 4/1987 | United Kingdom . | |
| 2207579 | 1/1989 | United Kingdom . | |
| 207579 | 2/1989 | United Kingdom | 128/696 |
| 8602538 | 9/1986 | WIPO . | |

OTHER PUBLICATIONS

NASA Tech Brief, 2301 NTIS Tech Notes, Springfield, VA, Feb. 1990, p. 196.

*Primary Examiner*—William E. Kamm
*Assistant Examiner*—Carl H. Layno
*Attorney, Agent, or Firm*—Ladas & Parry

[57] ABSTRACT

A sensor patch for attachment to a patient's body for obtaining physiological data from the patient and transmitting the physiological data to monitoring equipment. The sensor patch includes a structural support for supporting the sensor patch on the patient's body, a sensor for sensing physiological data from the patient's body, an adhesive for attaching the sensor patch to the patient's body, an electronics package including a power supply and circuitry for processing the sensed data to produce a conditioned signal, communications equipment for passing the sensed data from the sensor to the electronics package, and a transmitter for transmitting the conditioned signal from the sensor patch to the monitoring equipment. In a preferred embodiment, the electronics package and transmitter form part or parts of the sensor patch itself, and the sensor comprises one or more thermistors to sense the temperature of the patient's body. In another embodiment, the transmitter is an infra-red transmitter. There is also provided an ECG monitoring system incorporating the sensor patch.

13 Claims, 6 Drawing Sheets

SENSOR PATCH AND SYSTEM FOR PHYSIOLOGICAL MONITORING

BACKGROUND OF THE INVENTION

This invention relates to a sensor and system that is used to monitor and analyse electrocardiogram signals remotely from patients located in non-hospital sites.

As used herein, the term "electro-cardiogram" (ECG) refers to an electrical signal from the heart which may be measured from two or more sensors placed on the patients skin, either on a limb or about the patient's thorax.

The term "complex" refers to a period of ECG signal which, when voltage amplitude is plotted against time, exhibits a shape which may be repeated in other epochs. Typically, a complex will include a particular amplitude maxima or minima which is termed the detect point. The rate at which detect points occur in a particular ECG signal is the same as the heart rate. The term 'normal complex' refers to a complex in an ECG signal that is regularly repeated and is measured at electrodes placed on a person whose heart is beating in Normal Sinus Rhythm (NSR). The shape of a normal complex may vary from patient to patient and between ECG signals recorded from different sites on the same patient.

The terms P, Q, R, S and T when used herein in relation to ECG complexes refer to portions of a normal complex that relate to particular electro-physiological events in the cardiac cycle.

The term "normal rate" for a particular patient refers to a range of heart rates that is typical for a healthy individual of similar age to the patient when at rest.

The term "arrhythmia" relates to an abnormal rhythm of the heart that persists for multiple complexes which may or may not revert to normal sinus rhythm spontaneously. An arrhythmia may be made up of normal complexes at a rate that is abnormally high for the patient or abnormally low or, alternatively, an arrhythmia may consist of abnormal complexes at a high, low or normal rate.

In known systems, the patient is provided with sensors attached to the patient's body and which are coupled by electrical leads to an event recorder. The event recorder then sends the ECG signals to the monitoring system via a telecommunications line, e.g. a telephone line.

A major disadvantage of these known systems is that continuous monitoring of a patient has been met with a distinct lack of enthusiasm by the patient due to the need for a lead to connect the sensors to the event recorder. This causes discomfort and difficulties in dressing and washing, and also some embarassment as it is difficult to hide from view.

BRIEF SUMMARY OF THE INVENTION

It is an object of the present invention to provide a sensor and system whereby a patient can have their ECG monitored from home without requiring a visit by personnel skilled in the acquisition or interpretation of the ECG and which is comfortable and easy to wear and use.

Accordingly, in one aspect, the invention provides a sensor patch for attachment to a patient's body for obtaining physiological data from the patient and transmitting the physiological data to monitoring equipment, the sensor patch comprising a structural support member, sensing means for sensing physiological data from the patient's body, adhesive means for attaching the sensor patch to the patient's body, an electronics package including a power supply and circuitry for processing the sensed data to produce a conditioned signal, communication means for passing the sensed data from the sensing means to the electronics package, and a transmitter for transmitting the conditioned signal from the sensor patch to the monitoring equipment, wherein the electronics package and transmitter form part or parts of the sensor patch itself.

Preferably, the sensing means comprises a plurality of electrodes for sensing changes in electrical potential of the patient's body. The electrodes can be metallic, e.g. stainless steel, or they could be made of a silver chloride compound. A conductive paste is preferably provided as an interface between the electrodes and the skin of the patient.

Alternatively, or additionally, the sensing means could comprise one or more thermistors to sense the temperature of the patient's body.

The adhesive means preferably comprises a hydrogel compound which is electrostatically active and rehydrates itself. A preferred hydrogel compound contains salts which migrate between the skin of the patient and the sensors, thus reducing skin irritation due to maintenance of pH by the salt migration. Electrical balance is maintained since electrical conductivity is reduced as the moisture content of the hydrogel compound is reduced, which also reduces the pH.

The transmitter is preferably a radio transmitter, although microwave or infra-red transmitters could alternatively be used.

According to a second aspect of the invention, there is provided an ECG monitoring system comprising a sensor patch as described above for sensing and transmitting data representing an ECG signal of a patient, means for receiving the sensed data from the sensor patch at a primary site in the vicinity of the patient and for storing the sensed data, and means for sending the stored data from the primary site to a monitoring station where the ECG signal is monitored and analyzed.

In a preferred embodiment, the stored data is sent to the monitoring station at a central site via the standard voice telecommunications network.

Preferably, the central site is remote from the primary site and the monitoring station is preferably capable of receiving and monitoring data from a large number of primary sites. Preferably, the means for receiving the sensed data and the means for sending the stored data are within a portable unit, which can be easily carried around by the patient.

In a preferred embodiment, the portable unit also includes means for monitoring the received data to detect an abnormality in the sensed data, and means for alerting the patient that an abnormality has been detected.

The method of modulation and transmission of the ECG signal over the voice telecommunications network is well known in the prior art and does not form part of the present invention.

According to a further aspect of the invention, there is provided a monitoring station for monitoring and analysing ECG signals from a patient, the station comprising receiving means for receiving raw ECG data signals, first processing means coupled to the receiving means for processing the received raw ECG data to provide a standardised digital signal representative of the ECG data, recognition means coupled to the first processing means for recognising and storing a current characteristic complex in a cardiac cycle of the ECG data, storage means for storing a reference complex from the cardiac cycle of the same patient, comparing means coupled to the recognition means and the storage means for comparing the current characteristic complex stored in the recognition means with the reference complex stored in the storage means and producing a similarity index signal indicative of the degree of similarity between the current characteristic complex and the reference complex, analysing means coupled to the comparing means for analysing a current characteristic complex which has been matched with the reference complex to determine whether cardiac arrhythmia is present in the ECG data, and alarm means coupled to the analysing means for generating an alarm if the presence of a cardiac arrhythmia in the ECG data signals is detected.

In a preferred embodiment, the reference complex stored in the storage means is a normal complex. However, the storage means preferably stores, additionally or alternatively to the normal complex, one or more abnormal complexes of the cardiac cycle of the patient. Preferably, the comparing means compares the current characteristic complex with each of the stored reference complexes. In one preferred embodiment, the comparing means first compares the current characteristic complex with a normal reference complex stored in the storage means. If the similarity index signal indicates a lack of similarity between the current characteristic complex and the normal reference complex, then the comparing means compares the current characteristic complex with each abnormal reference complex, in turn, until the similarity index signal indicates a match. If the current characteristic complex does not match any of the stored reference complexes, then it is considered by a skilled operator and either discarded or entered in the storage means as another abnormal reference complex.

Although the monitoring station is usually used to monitor ECG signals from many patients at various sites remotely, the signals being sent to the monitoring station via a telecommunication system; it is equally applicable where a patient and the monitoring station are at the same site.

In an embodiment where the patient and monitoring station are conveniently at the same site and the patient is undergoing treatment using an automatic treatment device, such as an automatic drug delivery device, the alarm means is preferably coupled to a controller of the automatic treatment device so as to appropriately control the automatic treatment device according to whether a cardiac arrhythmia in the ECG data signals is detected. The automatic treatment device can be an automatic drug delivery system, such as an infusion pump, or could be an external pacemaker device or a de-fibrillation device.

Furthermore, although the monitoring station usually monitors only one ECG signal from a particular patient at a time, it can equally be used to monitor more than one ECG signal from one patient or ECG signals from multiple patients simultaneously. The monitoring station can also be used in systems that are capable of monitoring other physiological signals (including, but not limited to: blood pressure, spirometry signals and contractility signals) in addition to the ECG signal, as well as to systems which only monitor ECG signals.

Other advantages of the monitoring station according to the invention are:

1. It detects the presence of a dangerous cardiac state from the ECG automatically at the time that the ECG is being monitored.
2. It compares ECG signals recorded from a patient at different times in a way that allows an assessment as to whether the cardiac state of the patient has changed over time.
3. It provides an alarm if a new, pathological cardiac state develops in a patient so that assessment from an expert in the art of ECG interpretation may be obtained and/or medical intervention be initiated.

BRIEF DESCRIPTION OF THE DRAWINGS

Further features and advantages of the present invention will become more fully apparent from the detailed description of one embodiment of the invention given below, when read in conjunction with the accompanying drawings, wherein.

DETAILED DESCRIPTION OF THE ILLUSTRATIVE EMBODIMENT

Figure 1:
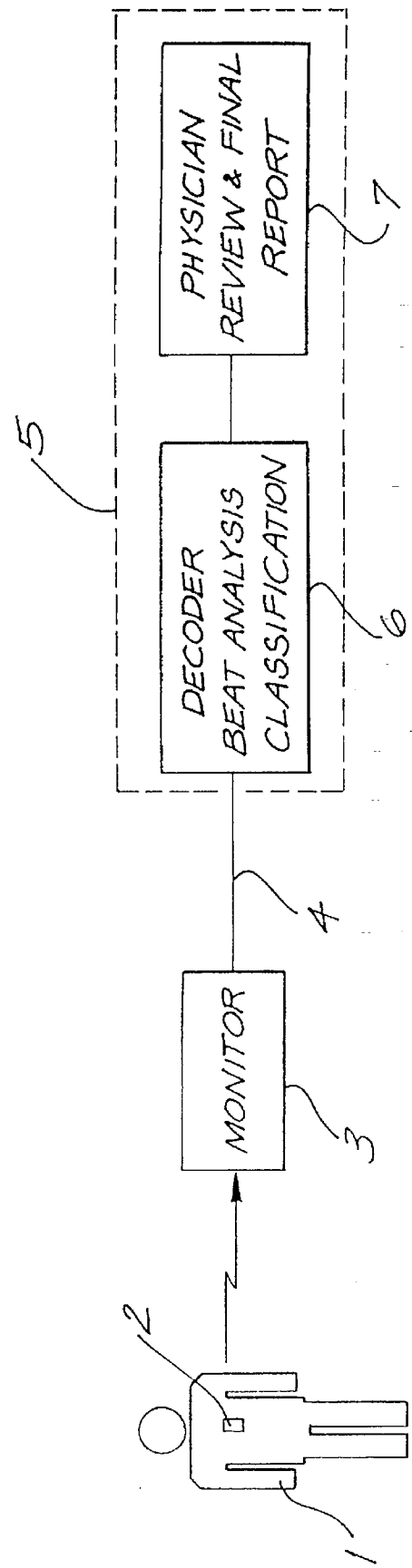
FIG. 1 is a schematic diagram of a sensing and analysing system according to one embodiment of the invention.

There is shown in FIG. 1, in block diagram form, a system for sensing and analysing ECG data signals from a patient to determine whether arrhythmia is present, and, if so, to produce an alarm. A patient 1 is provided with a sensor patch 2, of a type to be further described below, which is worn on the skin of the chest. The sensor patch includes a radio transmitter, as well as a power supply, and transmits ECG data signals, conditioned, as necessary, by suitable conditioning circuitry in the sensor patch, to a portable monitor unit 3.

The portable monitor unit 3 is designed to be easily carried around by the patient, preferably in a pocket, and includes a receiver for receiving the ECG data signals transmitted from the sensor patch 2. The unit 3 also includes circuitry for interfacing with a telephone line 4 to send the ECG data signals to a central monitoring station 5 by the telephone line 4. The portable unit 3 preferably also has monitoring circuitry for monitoring the incoming ECG data signal to determine whether there is any abnormality and to alert the patient if an abnormality in the ECG data signal is detected.

The central monitoring station 5 includes a part 6 that decodes the ECG data signals received from the portable unit 3 via the telephone line 4 and performs beat and rhythm analysis for classification of the ECG data. Periodically, data is reviewed by a professional skilled in the field and a report generated (7).

Figure 3:
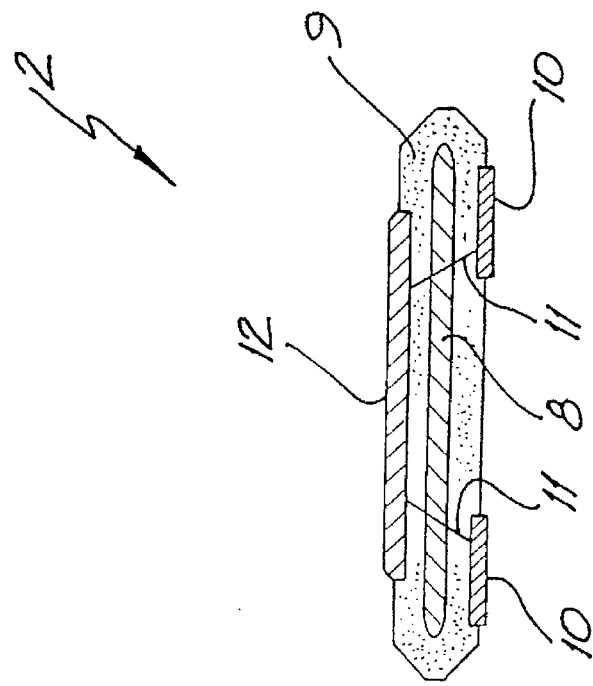
FIG. 3 is a schematic cross-sectional view through the sensor patch of FIG. 2.
Figure 2:
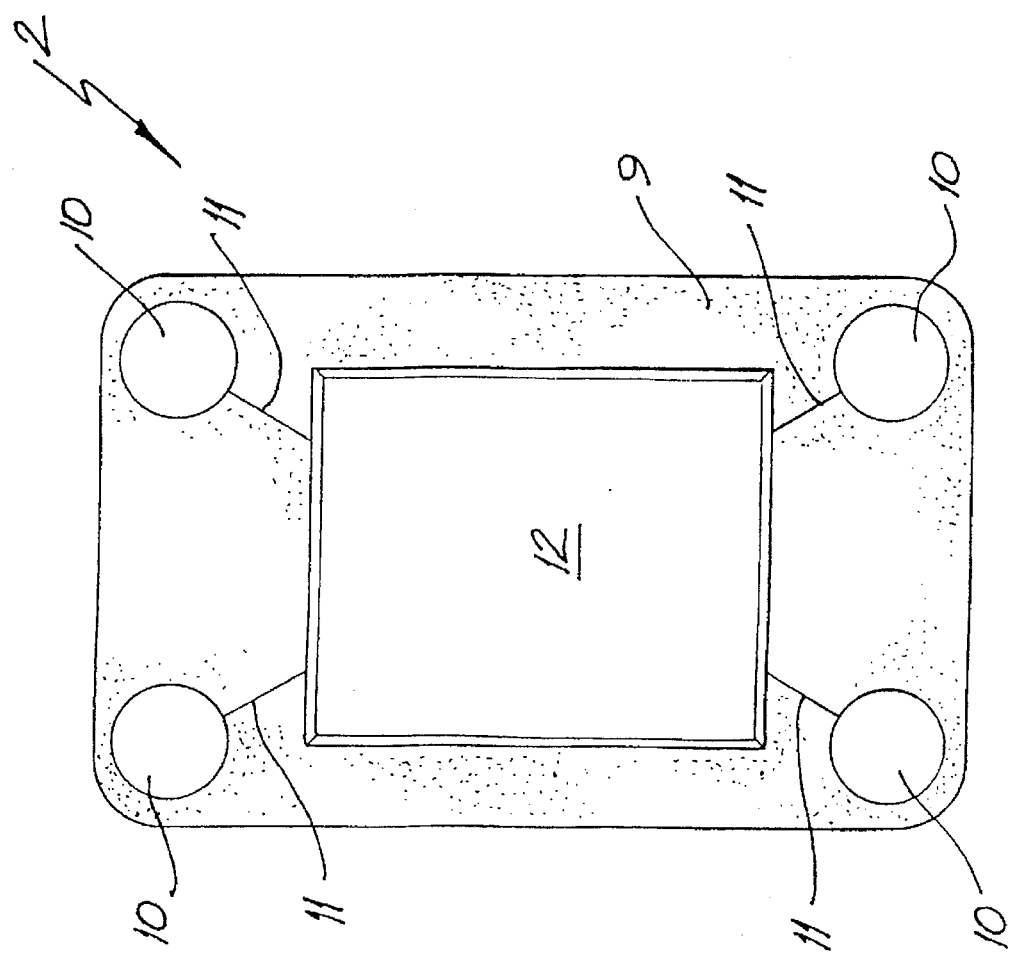
FIG. 2 is a schematic top plan view of a sensor patch used in the system of FIG. 1.

Turning now to FIGS. 2 and 3, the sensor patch 2 will be further described. The patch 2 is approximately the size of a playing card, for example 110 mm long by 70 mm wide and is approximately 10 mm thick. Thus, it can be easily worn by a patient without much discomfort. The patch comprises a central structural support member 8 formed of a flexible, but rigid, plastics material, such as Milar. The structural member 8 is surrounded by an adhesive gel 9 which is preferably a hydrogel compound. The hydrogel compound is a sticky jelly which contains salts, such as Sodium and Potassium. Provided the jelly is wet, the pH balance is maintained and the salts migrate between the skin of the patient and electrodes attached to the jelly and in contact with the skin. This migration of salts maintains the electrostatic balance and thereby reduces irritation. As the water content reduces, the pH and the electrical conductivity of the gel is reduced, thereby reducing the salt migration. By making sure that the patient wearing the patch has a bath or shower at least once a day, the gel becomes rehydrated and it is expected that such a patch will last and operate continuously for at least a week before its power supply is exhausted and it is thrown away.

The patch is provided with a number of electrodes 10, for example four, which are positioned on the gel 9 so as to contact the skin of the patient when the gel 9 adheres to the skin. A conductive paste may be used between the electrodes and the skin of the patient to improve the electrical conductivity therebetween. The electrodes 10 are either metallic, such as stainless steel, or formed of a silver chloride compound and are electrically connected by connections 11 to an electronic package 12.

The electronic package 12 includes a power supply, such as a small cell, circuitry for receiving signals from the electrodes 10, for conditioning the signals to provide a conditioned signal and a short range radio transmitter to transmit the conditioned signal to the portable monitor unit 3 which is nearby, and associated support circuitry. Thus, by having the radio transmitter at the same point as the sensors, the need for electrical signal lines from the sensor to a monitoring unit is avoided. As previously mentioned, the transmitter need not be radio, but could be microwave or infra-red, if in direct line of sight with the receiver in the portable unit.

The conditioning circuitry processes the signals from each electrode by filtering the signals and normalising according to measurements made when the respective electrode is disconnected. The normalised signals may also be compared to produce a difference signal representing the difference in potential sensed by different electrodes. Alternatively, the normalised signal from each electrode may be transmitted to the portable unit 3, where such comparisons are undertaken.

When the patient feels discomfort or concern, or if the portable unit gives an alarm, the patient telephones the central monitoring station and downloads the stored data from the portable unit via the standard telephone line. If required, the patient can also transmit current, real time ECG data so that it can be evaluated by the central station and any necessary action can be taken.

Figure 4:
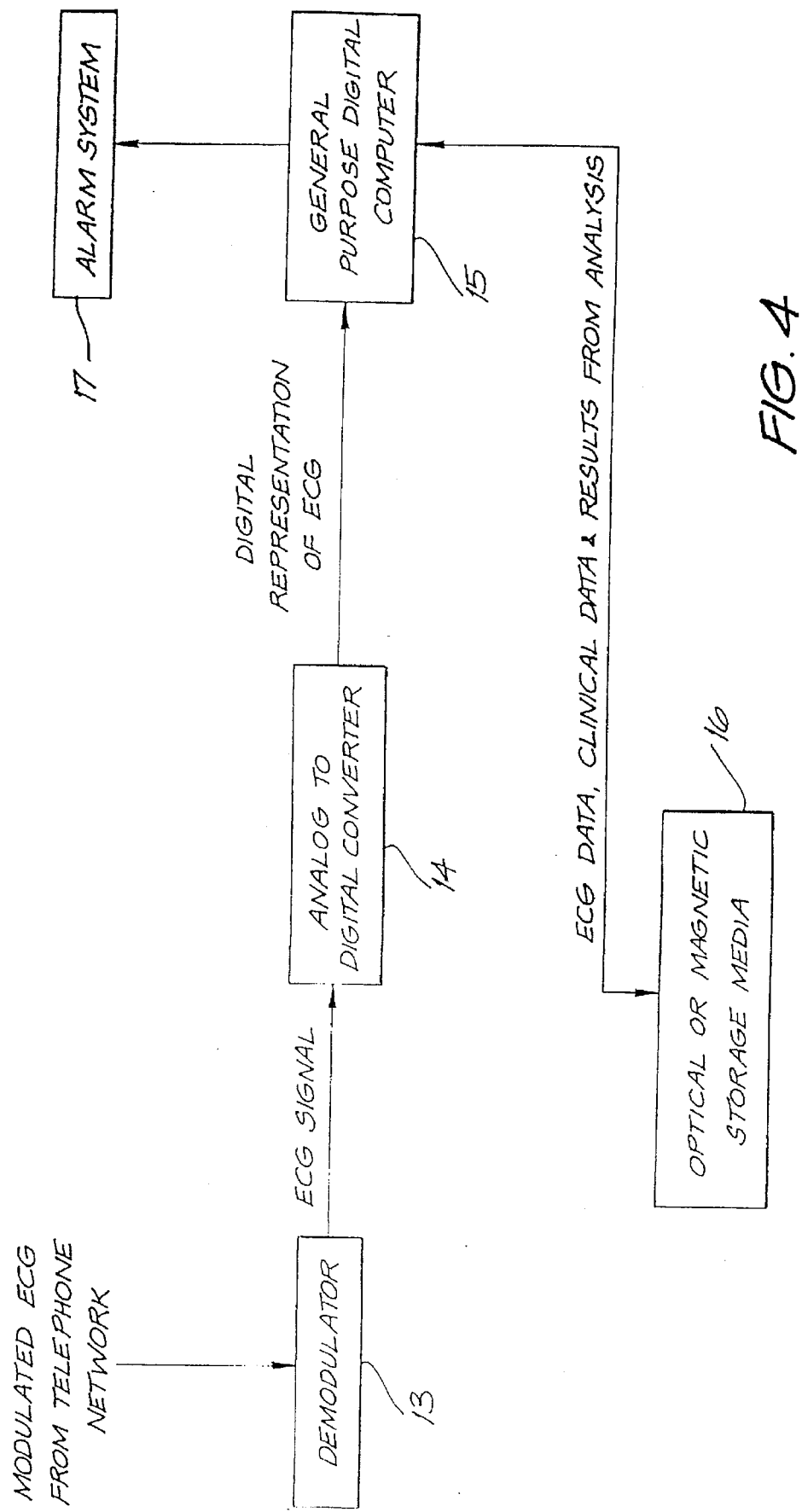
FIG. 4 is a schematic block diagram showing a monitoring station used in the system of FIG. 1.

FIG. 4 illustrates the interconnection of the hardware used at the Central Monitoring Station analysis site.

The modulated ECG signal from the telephone network is demodulated by demodulator 13. The signal is then digitized by an analogue to digital converter 14 at regular sampling intervals. The digital representation of the ECG signal is then input to a general purpose digital computer 15.

The combined gain of the demodulator 13 and analog to digital converter 14 may be automatically adjusted by the demodulator 13, analog to digital converter 14, the computer 15 or by any combination of these three. Connections for automatic gain control between these elements are not shown in FIG. 4.

The computer 15 processes the ECG data to decide if a dangerous cardiac event is occurring. The ECG data is also processed to extract information which may be stored in such a way that will allow tracking of the state of the patient's cardiac disease over prolonged periods. The storage media 16 which can be optical, magnetic or any other type, is used to store the digital representation of the ECG data and information derived from it, as well as patient identification data and clinical information.

When the analysis performed by the computer 15 indicates that a dangerous event is occurring in the ECG currently being processed, an alarm is raised by the alarm system 17. When an alarm is raised it is envisaged that the staff present at the analysis site would initiate medical intervention to alleviate the dangerous event.

Figure 5:
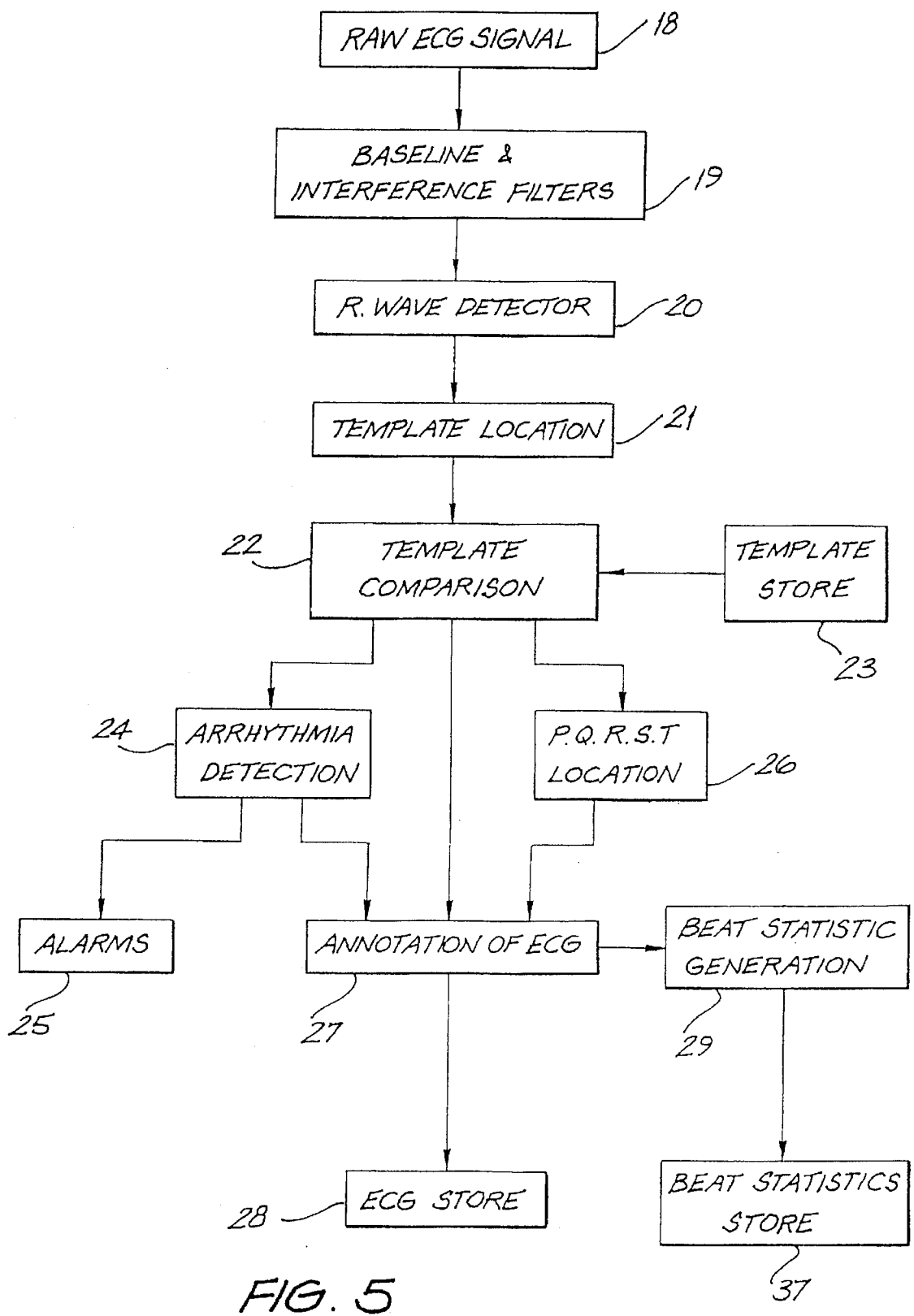
FIG. 5 is a flow diagram showing the processing carried out in the monitoring station of FIG. 4.

The processing of the ECG data takes place as shown in FIG. 5. In the illustrative embodiment of the invention, the sampled ECG signal 18 is initially processed by filters to remove baseline wander and mains frequency interference 19. The filters used in step 19 remove unwanted baseline wander and mains frequency interference without causing distortion of the shape of the underlying ECG complexes in the signal.

The filtered signal is then processed at step 20 to detect R wave points in time in the ECG signal. Portions of the signal either side of each R point together with the R point itself form a template which is located in the signal by the template location step 21. This template is then processed in comparison step 22.

The comparison step 22 compares the template in the current ECG signal, referred to as the test template and produces a number termed a "similarity index". The test template is extracted from the template store 23. If the similarity index produced by the comparison of the current template with the test template is above a predetermined threshold, a match is found. If not, the two templates do not match.

The test template and current template are coherent in time in so far as the R point occurs at the same duration from the start of each template.

The templates which may be used as test templates in the template store are generated for a particular patient when the patient is first presented to the system. Generation of test templates is illustrated in FIG. 6.

Figure 6:
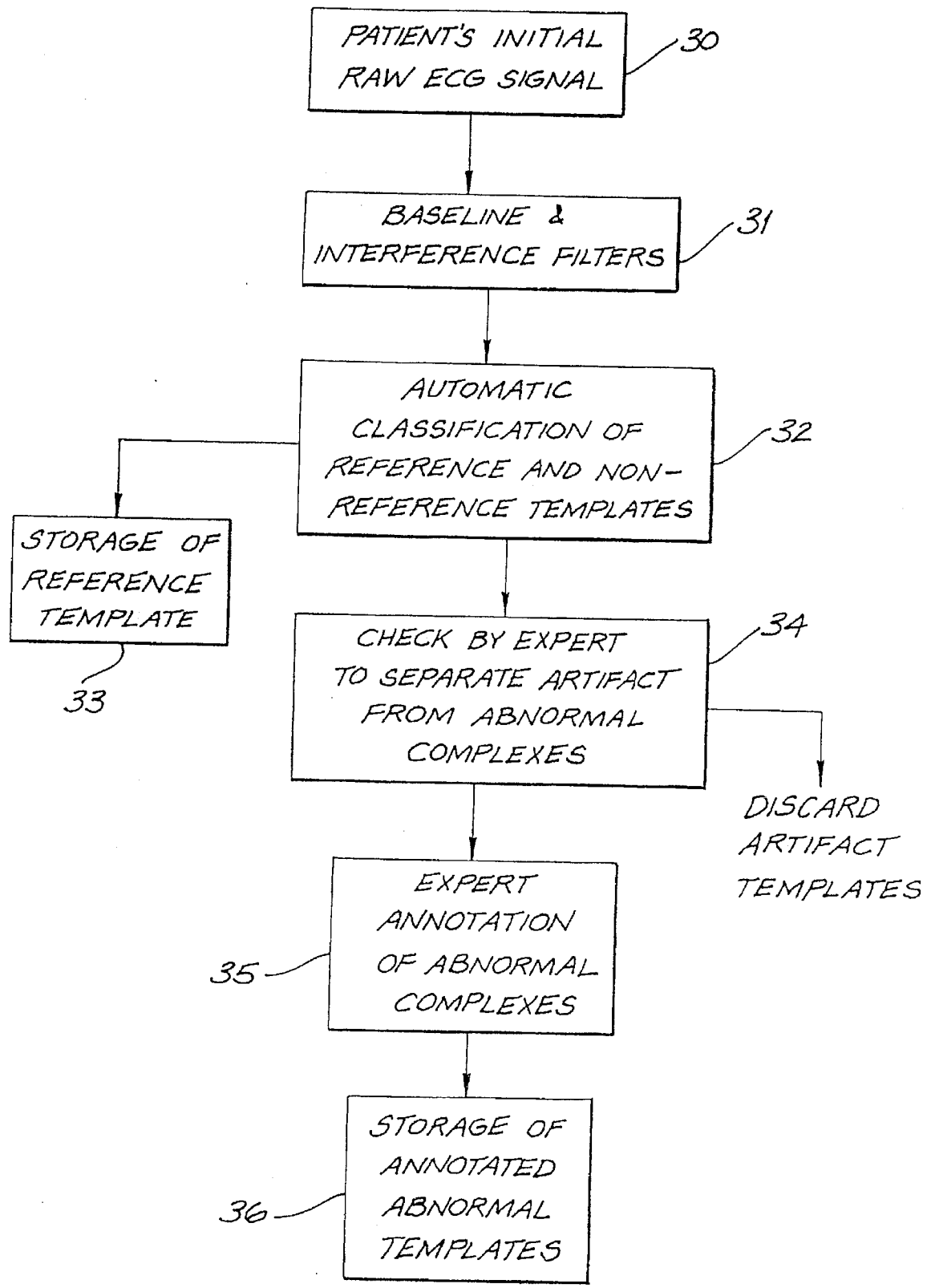
FIG. 6 is a flow diagram showing the flow of information which occurs when a patient is first presented to the system.

Referring now to FIG. 6, when a patient is first presented to the system the patients raw ECG signal 30 is again processed (31) by the baseline and interference filters. A representative ECG template is automatically generated (32) for this patient and stored in the template store 33. The representative template will match most the ECG complexes in the patient's first ECG signal recorded by the system. If the patient exhibits normal sinus rhythm, the representative template will represent a normal QRS complex with morphological perculiarities relevant to the particular surface lead used to record the ECG. In a patient that does not exhibit normal sinus rhythm, the representative template will reflect the morphological abnormalities present in most of the patient's ECG complexes.

Templates that do not match the representative template are then checked by an expert in the field of ECG interpretation and artifacts are separated (34) from legitimate abnormal complexes. Abnormal complexes exhibit an abnormal morphology for the patient (such as, but not limited to Ventricular Ectopic Beats from various foci) also can be stored as templates. These abnormal templates are then annotated (35) by the expert with labels that reflect the origin of the abnormal morphology. The annotated, abnormal complexes are then stored in the template store 36.

Once an initial ECG has been recorded from a patient, subsequent ECG recordings do not generate a new representative template. The recording of the initial ECG requires an operator skilled in the art of interpretation of ECG signals to ensure appropriate labelling of abnormal templates. Subsequent recordings from a patient do not require the presence of an operator with such skills.

Returning now to FIG. 5 illustrating the operation of the analysis system when a signal is received from a patient who has previously had an ECG recorded by the system, the comparison step 22 is initially used to compare in-coming complexes with the previously generated representative template. When a complex is found that does not match the representative template, the comparison step 22 then compares the unknown complex with each abnormal template for the patient in turn. In this way, the number of beats that are considered normal for the patient as well as the number and type of ectopic or abnormal beats can be automatically generated at the time that the ECG signal is being received.

If a complex is found that does not match the representative template nor any of the patient's abnormal templates, it is marked as unknown and at a later time can be discarded by the operator if it is considered to be an artifact or used to generate a new abnormal template for the patient. This can be done after the ECG containing the unknown template has been recorded by personnel with ECG interpretation skills.

After each complex has been categorized by the comparison algorithm, an arrhythmia detection step 24 determines if the patient is experiencing a cardiac arrhythmia. The arrhythmia detection step 24 determines the presence of an arrhythmia from the underlying heart rate and the type of beat as determined by the comparison step 22.

If a cardiac arrhythmia is detected by the arrhythmia detection step 24, an alarm is raised (25) and medical intervention can be instigated by staff at the analysis centre.

A parameter measuremeṁt procedure 26 is applied after the template comparison step 22. This procedure 26 detects fiducial points in each complex that matches the representative template and generates interval parameters relating to the P, Q, R, S and T points in the complex.

The ECG signal is then annotated (27) with the results from the comparison step 22, the arrhythmia detection step 24 and the P, Q, R, S, T location procedure 26.

The annotated ECG is then stored for later review of this analysis period in store 28.

Statistics, such as average, maximum, and minimum heart rate, numbers of different types of ectopic beats, types and durations of arrhythmic episodes and average complex parameter values are generated for the period of ECG analysed in step 29 and stored in store 37.

The statistical data and annotated ECG are recorded every time a patient transmits an ECG to the system. The stored information derived by the processing from the ECG's, ECG data itself as well as representative and abnormal templates can be reviewed at a later time. This information will provide a comprehensive history of the patient's cardiac disease state.

Thus, comprehensive ambulatory surveillance of cardiac sick and high risk patients can be carried out, whilst providing the patient with a greater degree of freedom than has been possible hitherto. It will, of course, be appreciated that, although only one particular embodiment of the invention has been described in detail, various modifications and improvements can be made to what has been described without departing from the scope of the invention.

Figure 7:
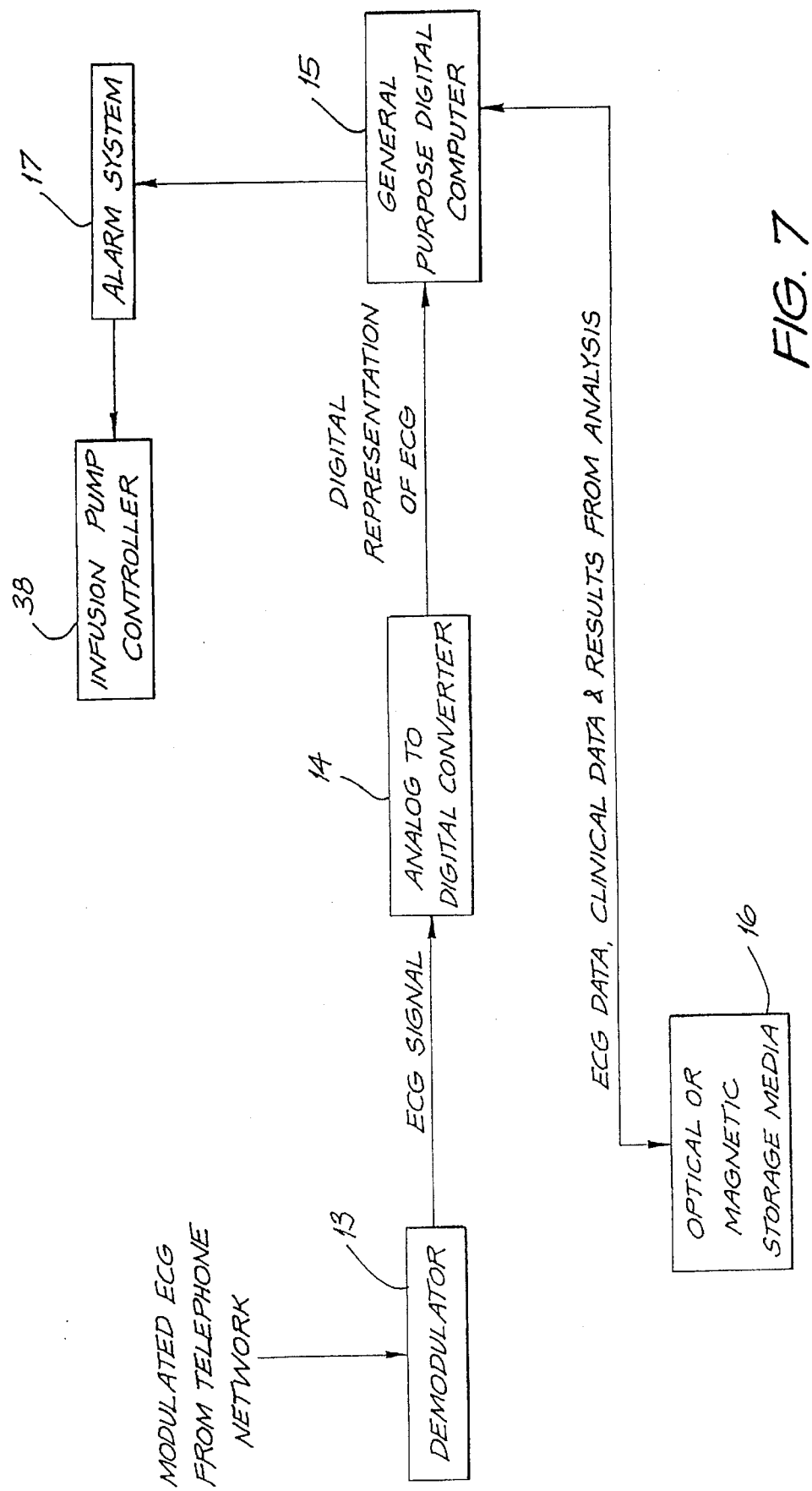
FIG. 7 is a schematic block diagram similar to that of FIG. 4, showing the alarm system used to control a drug delivery system.

For example, as shown in FIG. 7 in which the same elements have the same reference numerals as in FIG. 4, the alarm system 17 is coupled to a drug delivery system 38 so that the drug delivery system 38, for example, an infusion pump is appropriately controlled according to the presence or absence of arrhythmia.

We claim:

1. A sensor patch for attachment to a patient's body for obtaining physiological data from the patient and transmitting the physiological data to monitoring equipment, the sensor patch comprising structural support means for supporting the sensor patch on the patient's body, sensing means for sensing physiological data from the patient's body, adhesive means for attaching the sensor patch to the patient's body, an electronics package including a power supply and circuitry means for processing the sensed data to produce a conditioned signal, communication means for passing the sensed data from the sensing means to the electronics package, and a transmitter for transmitting the conditioned signal from the sensor patch to the monitoring equipment, wherein the electronics package and transmitter form part or parts of the sensor patch itself, and wherein the sensing means comprises one or more thermistors to sense the temperature of the patient's body.

2. A sensor patch for attachment to a patient's body for obtaining physiological data from the patient and transmitting the physiological data to monitoring equipment, the sensor patch comprising structural support means for supporting the sensor patch on the patient's body, sensing means for sensing physiological data from the patient's body, adhesive means for attaching the sensor patch to the patient's body, an electronics package including a power supply and circuitry means for processing the sensed data to produce a conditioned signal, communication means for passing the sensed data from the sensing means to the electronics package, and a transmitter for transmitting the conditioned signal from the sensor patch to the monitoring equipment, wherein the electronics package and transmitter form part or parts of the sensor patch itself, and wherein the transmitter is an infra-red transmitter.

3. A monitoring station for monitoring and analysing ECG signals from a patient, the station comprising receiving means for receiving raw ECG data signals, first processing means coupled to the receiving means for processing the received raw ECG data to provide a standardised digital signal representative of the ECG data, recognition means coupled to the first processing means for recognising and storing a current characteristic complex in a cardiac cycle of the ECG data, storage means for storing a reference complex from the cardiac cycle of the same patient, comparing means coupled to the recognition means and the storage means for comparing the current characteristic complex stored in the recognition means with the reference complex stored in the storage means and producing a similarity index signal indicative of the degree of similarity between the current characteristic complex and the reference complex, analysing means coupled to the comparing means for analysing a current characteristic complex which has been matched with the reference complex to determine whether cardiac arrhythmia is present in the ECG data, and alarm means coupled to the analysing means for generating an alarm if the presence of a cardiac arrhythmia in the ECG data signals is detected.

4. A monitoring station according to claim 3, wherein the reference complex stored in the storage means is a normal complex.

5. A monitoring station according to claim 3, wherein the storage means stores one or more abnormal complexes of the cardiac cycle of the patient.

6. An ECG monitoring system according to claim 3, wherein the alarm means is coupled to a controller of an automatic treatment device for treating the patient.

7. A monitoring station according to claim 3, wherein the comparing means compares the current characteristic complex with each of the stored reference complexes.

8. A monitoring station according to claim 7, wherein the comparing means first compares the current characteristic complex with a normal reference complex stored in the storage means and, if the similarity index signal indicates a lack of similarity between the current characteristic complex and the normal reference complex, then the comparing means compares the current characteristic complex with one or more stored abnormal reference complex, in turn, until the similarity index signal indicates a match.

9. An ECG monitoring system comprising a) a sensor patch for attachment to a patient's body for obtaining physiological data from the patient and transmitting the physiological data to monitoring equipment, the sensor patch comprising structural support means for supporting the sensor patch on patient's body, sensing means for sensing physiological data from the patient's body, adhesive means for attaching the sensor patch to the patient's body, an electronics package including a power supply and circuitry means for processing the sensed data to produce a conditioned signal, communication means for passing the sensed data from the sensing means to the electronics package, and a transmitter for transmitting the conditioned signal from the sensor patch to the monitoring equipment, wherein the electronics package and transmitter form part or parts of the sensor patch itself, and wherein said sensor patch is suitable for sensing and transmitting data representing an ECG signal of a patient, b) means for receiving the sensed data from the sensor patch at a primary site in the vicinity of the patient and for storing the sensed data, and c) means for sending the stored data from the primary site to a monitoring station where the ECG signal is monitored and analyzed.

10. An ECG monitoring system according to claim 9, wherein the stored data is sent from the primary site to the monitoring station at a central site via the standard voice telecommunications network.

11. An ECG monitoring system according to claim 10, wherein the central site is remote from the primary site and the monitoring station is capable of receiving and monitoring data from a large number of primary sites.

12. An ECG monitoring system according to claim 18, wherein the means for receiving the sensed data and the means for sending the stored data are within a portable unit.

13. An ECG monitoring system according to claim 12, wherein the portable unit also includes means for monitoring the sensed data to detect an abnormality in the sensed data, and means for alerting the patient that an abnormality has been detected.

\* \* \* \* \*